(12) United States Patent
Kukhanova et al.

(10) Patent No.: US 7,999,099 B2
(45) Date of Patent: Aug. 16, 2011

(54) MODIFIED 5'-PHOSPHONATE AZIDOTHYMIDINE—POTENTIAL ANTI-VIRAL PREPARATIONS

(76) Inventors: Marina Konstantinovna Kukhanova, Moscow (RU); Khandazhinskaya Anastasiya Lvovna, Moscow (RU); Maxim Vladimirovich Yasko, Moscow (RU); Elena Anatolievna Shirokova, Moscow (RU); Alexander Valerievich Shipitsyn, Malakhovka (RU); Andrey Georgievich Pokrovsky, Koltsovo (RU)

( * ) Notice: Subject to any disclaimer, the term of this patent is extended or adjusted under 35 U.S.C. 154(b) by 175 days.

(21) Appl. No.: 11/720,250

(22) PCT Filed: May 6, 2005

(86) PCT No.: PCT/RU2005/000249
§ 371 (c)(1),
(2), (4) Date: Mar. 10, 2008

(87) PCT Pub. No.: WO2005/062434
PCT Pub. Date: Jun. 15, 2006

(65) Prior Publication Data
US 2009/0111979 A1 Apr. 30, 2009

(30) Foreign Application Priority Data
Nov. 25, 2004 (RU) ................................ 2004134388

(51) Int. Cl.
*C07H 19/10* (2006.01)
*A61K 31/70* (2006.01)

(52) U.S. Cl. ........................................ 536/26.8; 514/51
(58) Field of Classification Search .................. None
See application file for complete search history.

(56) References Cited

U.S. PATENT DOCUMENTS

| | | | | |
|---|---|---|---|---|
| 4,824,850 A | * | 4/1989 | Bodor | 514/270 |
| 4,968,788 A | * | 11/1990 | Farquhar | 536/25.31 |
| 5,002,935 A | * | 3/1991 | Bodor | 514/58 |
| 5,413,996 A | * | 5/1995 | Bodor | 514/169 |

FOREIGN PATENT DOCUMENTS

| | | |
|---|---|---|
| WO | WO91/19727 A1 * | 12/1991 |
| WO | WO92/00988 A1 * | 1/1992 |

OTHER PUBLICATIONS (R) Shirokova et al. (I), "Uncharged AZT and D4T Derivatives of Phosphonoformic and Phosphonoacetic Acids as Anti-HIV Pronucleosides," Journal of Medicinal Chemistry, 47(14), 3606-3614 (2004); Web publ. May 29, 2004.*
(S) Shirokova et al. (II), "New Phosphonoformic Acid Derivatives of 3'-Azido-3'-deoxythymidine," Russian Journal of Bioorganic Chemistry, 30(3), 242-249 (2004): for Abstract see CAPLUS Search Notes; Answer 7 of 10.*
(T) Shirokova et al. (III), "New Lipophilic Derivatives of AZT and d4T 5'-Phosphates," Nucleosides, Nucleotides & Nucleic Acids, 22(5-8), 981-985 (2003); CAPLUS entry date: Sep. 11, 2003: for Abstract see Search Notes; Answer 9 of 10.*
(U) Orlov et al., "Investigation of Nucleoside and Nucleotide Derivatives by Plasma Desorption Mass Spectrometry," Molekulyarnaya Biologiya (Moscow),. 28(3), 708-713 (1994): for Abstract see CAPLUS Search Notes: Answer 10 of 10.*
(V) Casara et al., "Synthesis of Acid Stable 5'-o-fluoromethylphosphonates of Nucleosides. Evaluation as Inhibitors of Reverse Transcriptase," Bioorganic & Medicinal Chemistry Letters, 2(2), 145-148 (1992); only Abstract supplied.*

* cited by examiner

*Primary Examiner* — Lawrence E Crane
(74) *Attorney, Agent, or Firm* — Porter, Wright, Morris & Arthur, LLP

(57) ABSTRACT

The invention relates to the field of molecular biology, virology and medicine and, more specifically, to novel derivatives of 3'-azido-3'-deoxythymidine phosphonates with the following general formula

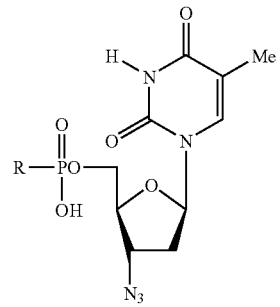

where R=alkyl groups, including those containing halogen atoms, carboxy-, hydroxy-, alkoxy- and acyloxy- groups as well as substituted aminocarbonyl groups. The compounds can be used as antiviral agents as they have low toxicity and can effectively inhibit replication of type 1 immunodeficiency virus in MT-4 cell culture and generate AZT in mammalians ensuring a gradual increase of its concentration in the blood.

1 Claim, No Drawings

MODIFIED 5'-PHOSPHONATE AZIDOTHYMIDINE—POTENTIAL ANTI-VIRAL PREPARATIONS

CROSS-REFERENCE TO RELATED APPLICATIONS

This application is a U.S. National phase of International Patent Application Number PCT/RU2005/000249 filed on May 6, 2005 which claims priority from Russian Patent Application Number RU 2004134388 filed on Nov. 25, 2004.

FIELD OF THE INVENTION

The present invention relates to the field of molecular biology, virology and medicine and, more specifically, to novel derivatives of nucleosides, namely, to substituted 5'phosphonates of AZT. These compounds possess an antiviral effect and may be used to suppress reproduction of the human immunodeficiency virus.

BACKGROUND OF THE INVENTION

At present a whole range of compounds possessing antiviral activity against HIV are used in practical medicine. They include nucleoside and non-nucleoside inhibitors. The most frequently used nucleoside derivatives include 3'-azido-3'-deoxythymidine (AZT, Zidovudine), 2',3'-dideoxycytidine (ddC, Zalcitabine, 2',3'dideoxyinosine (ddI, Didanosine), 2',3'-dideoxy-2',3'-didehydrothymidine (d4T, Stavudine and 2',3'-dideoxy-3'-thiacytidine (3TC, Lamivudine) [De Clercq, E., 2002. New development in anti-HIV chemotherapy. *Biochim. Biophys. Acta,* 1587 258-275].

The mechanism of action of the above compounds comprises its diffusion into infected cells, where they undergo triphosphorylation and specifically inhibit DNA synthesis catalyzed by HIV reverse transcriptase. High variability of HIV results in rapid emergence of resistant strains of the virus [Groschel, B., Cinatl, J. H., and Cinatl J. Jr., 1997. Viral and cellular factors for resistance against antiretroviral agents. *Intervirology,* 40, 400-407; Antonelli, G, Turriziani, O., Verri, A., Narciso, P., Ferri, F., D'Offizi, G., and Dianzini, F., 1996. Long-term exposure to zidovudine affects in vitro and in vivo the efficiency of thymidine kinase. *AIDS Res Hum Retrovir.,* 12, 223-228] and, hence to the necessity of changing medication. Besides, due to low efficacy of intracellular transformations currently used drugs have to be administered in high doses leading to pronounced toxic effects.

AZT toxicity causes suppression of the activity of spinal cord cells, liver function impairment and myopathy [Chariot, P., Drogou, I., De Lacroix-Szmania, I., Eliezer-Vanerot, M. C., Chazaud, B., Lombes, A., Schaeffer, A., and Zafrani, E. S., 1999. Zidovudine-induced mitochondrial disorder with massive liver steanosis, myopathy, lactic acidosis, and mitochondrial DNA depletion. *J. Hepatol.* 30, 156-160; Kellam, P., Boucher, C. A., and Larder, B. A., 1992. Fifth mutations in HIV reverse transcriptase contributes to the development of high level resistance to zidovudine. Proc. Natl. Acad. Sci. U.S.A, 89, 1934-1938; Ren, J., Esnouf, R. M., Hopkins, A.L., Jones, E. Y., Kirby, I., Keeling, J., Ross, C. K., Larder, B. A., Stuart, D. I., and Stammers, D. K., 1998. 3'-Azido-3'-deoxythymidine drug resistance mutations in HIV-1 reverse transcriptase can induce long range conformational changes. *Proc. Natl. Acad. Sci. U.S.A,* 95, 9518-9523]. Rapid elimination of AZT from the body necessitates frequent administration. Besides, resistant strains of the virus develop rather soon during long-term treatment with AZT and the therapy loses its efficacy. Despite all the above disadvantages AZT still remains the most widely used anti-HIV drug.

The known H-phosphonate of AZN (Nikavir®) approved for AIDS treatment in Russia is less toxic than AZT [Intracellular metabolism and pharmacokinetics of 5'-hydrohenphosphonate of 3'-azido-2',3'-dideoxythymidine, a prodrug of 3'-azido-2',3'-dideoxythymidine. Antiviral Research 63 (2004), 107-113]. The effect of Nikavir is based on its ability to release AZT which, after intracellular transformation to AZT-5'-triphosphate inhibits the replication of HIV. According to pharmacokinetic research data, clinical advantages of Nikavir are due to slower and more gradual increase of AZT concentration in the blood than in case of administration of proper AZT; $C_{max}$ of AZT from Nikavir being less than $C_{max}$ of AZT from Zidovudine, and $T_{1/2}$ of AZT from Nikavir being greater than $T_{1/2}$ of AZT from Zidovudine [Y. Skoblov et al./Antiviral Research 63 (2004) 107-113]. Nevertheless, the toxicity of Nikavir remains rather high. Another disadvantage consists in the development of resistance to Nikavir.

Some other AZT derivatives were synthesized and evaluated as anti-HIV agents. Among them there are 5'-alkylphosphonyl AZT (alkyl is $C_1$ to $C_8$) [A. A. Kraevsky et al W091/19727 and N. S. Bodor W092/00988], 5'-fluoromethylphosphonyl, 5'-difluoromethylphosphonyl, 5'-fluorocloromethylphosphonyl- and 5'-trifluoromethylphosphonyl-AZT [P. J. Casara et at Biorganic Med. Chem. Letters, 2(2) (1992) 145-148]. Earlier physicochemical properties of 5'-hydroxymethyl- and 5'-iodomethylphosphonyl AZT were reported [V. M. Orlov et al, Molekulayrnaya Biologia (Moscow), 28(3) (1994) 708-713]. In addition, chemical synthesis of 5'-R-phosphonyl-AZT where R=—H₂C(O)NH₂, —C(O)NH₂, —C(O)NHCH₃, —C(O)NHCH₂CH₂Ph,

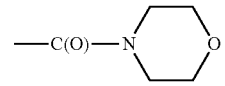

was described [E. A. Shirokova et al, Nucleosides, Nucleotides&Nucleic Acids 22(5-8) (2003) 981-985; E. A. Shirokova et al, Russian Journal of Bioorganic Chem. 30(3) (2004) 242-249; E. A. Shirokova et al, J. Med. Chem. 47(14) (2004) 3606-3614.], however their biological properties were not studied.

DESCRIPTION OF THE INVENTION

The present invention solves the task of low-toxicity derivatives of AZT capable of penetrating into the cell and gradually releasing the active nucleoside (AZT). This will make it possible to maintain therapeutically sufficient intracellular concentration of the drug for a prolonged period and thus reduce the single dose of the drug and/or frequency of administration and abate side effects.

The task is solved by creating 5'-phosphonyl-3'-azido-3'-deoxythymidine compounds with the follow general formula:

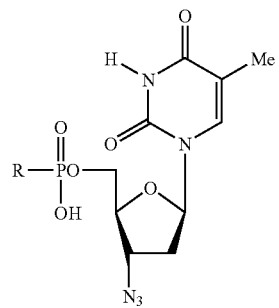

R=alkyl groups, including those containing halogen atoms, carboxy-, hydroxy-, alkoxy-and acyloxy-groups as well as substituted aminocarbonyl groups.

The novel compounds inhibit reproduction of type 1 human immunodeficiency virus in MT-4 lymphocyte cell line, protect the cells from cytopathogenic action of the virus and do not demonstrate toxicity towards host cells up to extremely high concentrations (Table 1). Experimental data confirm that while producing no toxic effect on the cells in effective concentrations (50% toxic doses are 2-4 orders greater than 50% inhibiting doses) the investigational compounds, the investigational compounds demonstrate a high degree of type 1 immunodeficiency virus in MT-4 cell culture. Therapeutic indexes of the investigational compounds calculated as the ratio of the therapeutic dose of the drug to its effective dose are comparable to those of AZT H-phosphonate. Virological tests were performed according to previously described protocols.

It has been demonstrated that in dogs phosphonates of AZT slowly release AZT, thus representing latent forms of AZT (Example 7, Table 2). Studies demonstrate that for all the phosphonates covered by this application the only metabolite detectable in animal blood is AZT. Pharmacokinetic parameters included in Table 2 were determined based on generated AZR and depended on the phosphonate structure.

BEST EXAMPLES OF IMPLEMENTATION OF THE INVENTION

The target phosphonates were produced using the following scheme:

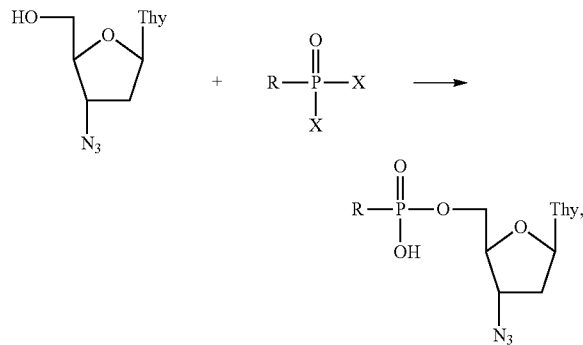

Where X=Cl or OH
Ia: R=ClCH$_2$
Ib: R=ICH$_2$
Ic: R=HOCH$_2$
Id: R=CH$_3$OCH$_2$
Ie: R=H$_2$NC(O)

Specific examples below reveal the essence of the invention.

EXAMPLE 1

5'-Chloromethylphosphonyl-3'-azido-3'-deoxythymidine (Ia).

Cloromethyl phosphonidyl dichloride (0.92 ml, 9 mM) was added to the solution of 3'-azido-3'-deoxythymidine (0.8 g, 3 mM) in triethyl phosphate (10 ml) cooled to 0°C. The mixture was stirred for 18 hours at 18° C., diluted with a cooled mixture of pyridine (10 ml) and water (10 ml), stirred for 30 minutes and added to water (700 ml). The solution was injected into a column with DEAE cellulose and eluted in a linear gradient of NH$_4$HCO$_3$ (0☐15 mM, pH 7.5). Target fractions were evaporated, the residue was diluted with water (3 ml) and additionally purified on a LiChroprep RP-18 column using water as eluent. The target fraction was lyophilized obtaining 1 g (90%) of phosphonate (Ia). $^1$H NMR (D$_2$O): 7,72 q (1H, J=0,5 Hc, H-6), 6,27 t (1H, J=6 Hc, H-1'), 4,55 m (1H, H-3'), 4,21 m (3H, H-4', H-5'), 3,58 d (2H, J=8,5 Hc, CH$_2$-P), 2,54 m (2H, H-2'), 1,95 d (3H, J=0,5 Hc, CH$_3$). $^{31}$P NMR: 16,03 s.

EXAMPLE 2

5'-Iodomethylphosphonyl-3'-azido-3'-deoxythymidine (Ib)

5'-Iodomethylphosphonyl-3'-azido-3'-deoxythymidine (Ib) was synthesized from 3'-azido-3'-deoxythymidine and iodomethylphosphonic acid using the method described for compound Ia. The yield was 54%. $^1$H NMR (D$_2$O): 7,55 s (1H, H-6), 6,07 t (1H, J=6 Hc, H-1'), 4,37 m (1H, H-3'), 4,00 m (3H, H-4', H-5'), 2,89 (2H, J=9 Hc, CH$_2$-P), 2,34 m (2H, H-2'), 1,75 s (3H, CH$_3$). $^{31}$P NMR: 17,00 s.

EXAMPLE 3

5'-Hydroxymethylphosphonyl-3'-azido-3'-deoxythymidine (Ic)

Solution of acetoxymethylphosphonic acid pyridinic salt (1.2 mM) in pyridine (3 ml) was added to the solution of 3'-azido-3'-deoxythymidine (267 g, 1 mM) in pyridine, dicyclohexyl carbodiimide (520 mg, 2.5 mM) was added while stirring, the reaction mix was stirred for 10 hours at room temperature and diluted with water (5 ml). After stirring for 30 more minutes the sediment was separated and the solution was evaporated, the residue was dissolved in 1 M KOH (5 ml) and stirred for 5 hours at room temperature. The solution was evaporated and the residue was dissolved in water (100 ml). The solution was injected into a column with DEAE cellulose in the HCO$_3$ form and eluted in a linear gradient of NH$_4$HCO$_3$ (0☐15 mM, pH 7.5). Target fractions were evaporated, and re-evaporated with water (5 ml Ч3 times), the residue was diluted with water (3 ml) and chromatographed on a LiChroprep RP-18 column using water as eluent. The target fraction was lyophilized obtaining 238 mg (66%) of phosphonate (Ic).
$^1$H NMR (D$_2$O): 7,68 q (1H, J=0,5 Hc, H-6), 6,22 t (1H, J=6 Hc, H-1'), 4,48 m (1H, H-3'), 4,16 m (3H, H-4', H-5'), 3,77 d (2H, J=7 Hc, CH$_2$—P), 2,51 t (2H, J=6 Hc, H-2'), 1,93 d (3H, J=0,5 Hc, CH3). $^{31}$P NMR: 16.03 s.

EXAMPLE 4

5'-Methoxymethylphosphonyl-3'-azido-3'-deoxythymidine (Id)

5'-methoxymethylphosphonyl-3'-azido-3'-deoxythymidine was synthesized from 3'-azido-3'-deoxythymidine and methoxymethylphosphonic acid using the method described for compound Ic. $^1$H NMR (D$_2$O): 7,66 q (1H, J=0,5 Hc, H-6), 6,21 t (1H, J=6 Hc, H-1'), 4,48 m (1H, H-3'), 4,15 m (3H, H-4', H-5'), 3,68 q (2H, J=8 Hc, CH$_2$-P), 2,52 t (2H, J=6 Hc, H-2'), 1,94 d (3H, J=0.5 Hc, CH$_3$). $^{31}$P NMR: 16,03 s.

EXAMPLE 5

5'-Aminocarbonylphosphonyl-3'-azido-3'-deoxythymidine (Ie).

5'-Aminocarbonylphosphonyl-3'-azido-3'-deoxythymidine (Ie) was synthesized from 3'-azido-3'-deoxythymidine and aminocarbonylphosphonic acid using the method described for compound Ic obtaining 70 mg (94%) of compound Ie. $^1$H NMR (DMSO-d$_6$): 7,82 s (1H, H6), 7,17 s, 7,13 s (2H, NH$_2$), 6,12 t (1H, J 6,9, H1'), 4,5 m (1H, H3'), 3,95 m (3H, H4', H5'), 2,30 m (2H, H2'), 1,81 s (3H, CH$_3$). $^{31}$P NMR: (DMSO-d$_6$): −1,56 s. Mass-spectrum: m/e 374,3 [M$^+$].

EXAMPLE 6

Inhibition of HIV replication was studied by cultivating pre-infected lymphoid cells of MT-4 cell line in the presence of the investigational compounds in the concentration of 0.001-100 □g per 1 ml of culture medium during one passage, i.e. 4 days.

Inhibition of HIV replication in a sensitive cell culture is assessed by the reduction of p24 virus-specific protein accumulation (according to immunoenzyme assay) as well as by the increase of cell viability in the presence of the drug as compared to the control on the 4$^{th}$ day of cultivation using bromide 3-(4,5-dimethylthiasol-2-yl)-2,5-diphenuyltetrasolium (MTT).

Assessment of Cytotoxicity of the Compounds

Drug cytotoxicity is assessed by adding its dilutions in serum-free RPMI-1640 medium to MT-4 cell suspension (initial concentration in the wells of a 96-well plate (Cel-Cult, UK) to final concentrations of 0.001-100 □g/ml (3 wells per dose) and cultivating at 37° C. for 4 days. Inoculation concentration is 0.5·10$^6$ cells/ml is used. Cells in the same volume serum-free medium containing no drug are used as control. Viable cells are counted on the 4$^{th}$ day of cultivation using the formasan method (MTT staining of live cells). Toxicity of various doses of the drug is assessed by comparing cell viability with the control, the results are used to plot the dose-dependent curve and determine the concentration reducing cell viability by 50% (CD$_{50}$). Effective concentrations of the investigational compounds produce on toxic effect on MT-4 cells. It should be noted that 50% toxic doses are 5-6 orders higher than does effective against HIV-1 (table 1).

The effect of the investigational compounds of HIV-1 replication in MT-4 cell culture was studied using a known method.

The therapeutic index, or the index of selectivity (IS), is calculated as the ratio of 50% toxic concentration of a compound to its 50% effective dose (the results are presented in table 1). Based on these quantitative inhibition indexes it is possible to judge antiviral efficacy of the compounds according to this application which consists in a high degree of suppression of HIV-1 replication in MT-4 cell culture comparable to that of Nikavir.

EXAMPLE 7

A dog weighing 12 kg was orally given 250 mg of the investigational compound (mixed with curd). Blood samples (1 ml) were taken at defined intervals from the femoral vein. The samples were centrifuged (10 minutes at 2000 rpm) and the supernatant was separated. Oxetan (internal standard, 0.25 □g) and methanol (0.75 ml) were added to aliquots of the supernatant (0.25 ml). The resulting mixture was centrifuged for 3 minutes at 5000 rpm. The supernatant was separated and evaporated in air flow at 40° C., water (1 ml) was added to the residue. Aliqutes (20□1) were analyzed by HPLC in Gynkotec chromatograph (Germany) using Ultrasphere ODC Beckman analytical column (USA). Eluent: 6% acetonitrile in 0.1% H$_3$PO$_4$ (pH 2.1) in the presence of 0.15% triethylamine; detection at □$_{max}$ 265 nm at 30° C. Pharmacokinetic parameters obtained at a result of analyzing the data are presented in table 2.

TABLE 1

Antiviral activity of AZT phosphonates against GKV-4046 HIV-1:

| Compound | CD$_{50}$, μM | ID$_{50}$, μM | IS |
|---|---|---|---|
| Ia | 300 | 0.05-0.1 | >3000 |
| Ib | >500 | 1-5 | >100 |
| Ic | >500 | 0.08-0.3 | >1600 |
| Id | >500 | 1-5 | >100 |
| Ie | >300 | 0.05-0.1 | >3000 |
| Nikavir | 260 | 0.13 | 2015 |

TABLE 2

Pharmacokinetic parameters of azidothymidine after oral administration of 250 mg of substances of AZT, Nikavir, and compounds Ia and Ie in the amount equivalent to 250 mg of AZT.

| Compound | T$_{1/2}$ hours | AUC, mg × h/ liter | MRT, hours | CL, liter/ hour | T$_{max}$, hours | C$_{max}$, mg/ liter |
|---|---|---|---|---|---|---|
| Ie | 9.6 | 9.24 | 13.9 | 27.0 | 5.0 | 0.74 |
| Nikavir | 7.2 | 16.6 | 10.4 | 15.0 | 4.0 | 1.89 |
| AZT | 5.2 | 58.8 | 7.5 | 4.2 | 2.5 | 9.77 |

Thus, it has been demonstrated that the compounds included in the application have low toxicity and can effectively inhibit replication of type 1 immunodeficiency virus in MT-4 cell culture and generate AZT in mammalians ensuring a gradual increase of its concentration in the blood.

What is claimed is:

1. An AZT 5'-phosphonate of the formula:

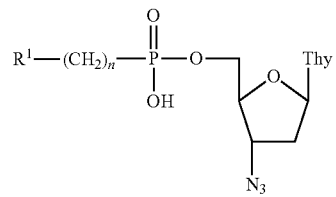

wherein one of: (i) when n=0-2, R$^1$=R$^2$—NH—C(O)— and R$^2$ is selected from the group consisting of H, alkyl C$_1$-C$_6$, cycloalkyl C$_5$-C$_7$, and arylalkyl, and (ii) when n=1-2, R$^1$ is selected from the group consisting of Cl—, Br—, I—, CH$_3$CO—, NC—, and N$_3$—.

* * * * *